United States Patent [19]
Dureault et al.

[11] Patent Number: 5,450,194
[45] Date of Patent: Sep. 12, 1995

[54] OPTICAL MEASURING DEVICE, PARTICULARLY USING SPECTROPHOTOMETRY

[76] Inventors: Bernard Dureault, 126 Rue de la Pompe, Paris 16; Jacques Lordet, 9 Rue de Paris, 94100 St. Maur; Claude Bonnejean, 2 Allie du Bois Deué, 91080 Courcouronnes, all of France

[21] Appl. No.: 210,126

[22] Filed: Mar. 17, 1994

[30] Foreign Application Priority Data

Apr. 6, 1993 [FR] France .................. 93 04050

[51] Int. Cl.⁶ .............. G01J 3/42; G01J 3/08
[52] U.S. Cl. .................................. 356/319
[58] Field of Search .......... 356/319, 323, 325; 385/19

[56] References Cited

U.S. PATENT DOCUMENTS

| | | | |
|---|---|---|---|
| 4,726,646 | 2/1988 | Tanaka et al. | 385/19 |
| 4,820,045 | 4/1989 | Boisde et al. | 356/319 |
| 5,201,016 | 4/1993 | Jinbo et al. | 385/19 |
| 5,210,590 | 5/1993 | Landa et al. | 356/319 |

FOREIGN PATENT DOCUMENTS

| | | |
|---|---|---|
| 0062160 | 3/1982 | European Pat. Off. . |
| 0177387 | 8/1985 | European Pat. Off. . |
| 2622305 | 10/1987 | France . |
| 2200222 | 7/1988 | United Kingdom . |
| 8300384 | 2/1983 | WIPO . |
| 9215912 | 9/1992 | WIPO . |

*Primary Examiner*—Vincent P. McGraw
*Assistant Examiner*—K. P. Hantis

[57] ABSTRACT

An optical measuring device, particularly using spectrophotometry, which comprises at least one group of optical fibers (24) connected to measuring cells, at least one auxiliary optical fiber (30) and at least one selection member connecting the latter to the group. The selective member establishes a link between the auxiliary fiber and one of the fibers of the group. The selection member comprises fixed optical means (32, 34) for establishing the link between the group and the auxiliary fiber and retractable seals (36) associated with the fibers of the group and which seal the ends of auxiliary fibers leading to said member.

5 Claims, 3 Drawing Sheets

OPTICAL MEASURING DEVICE, PARTICULARLY USING SPECTROPHOTOMETRY

BACKGROUND OF THE INVENTION

The present invention relates to an optical measuring device, particularly using spectrophotometry. The invention is more particularly applicable to the field of nuclear chemistry.

During spectrophotometric measurements in the ultraviolet, visible or infrared ranges, use is made of equipment in which samples to be analyzed are placed in measuring cells and are traversed by an ultraviolet, visible or infrared beam.

In certain cases, it is difficult or even impossible to transfer the samples into the measuring cells. For example, this is the case with measurements performed in shielded enclosures with radioactive solutions. It is often impossible or at least difficult to install equipment in such enclosures.

An optical coupling device has been developed, which makes it possible to pass the light beam from a spectrophotometer to a sample to be measured and then return the light beam to the spectrophotometer after it has traversed the sample. This device is an assembly which is relatively complex with respect to the components and optical fibers. It only makes it possible to carry out a measurement at a single point (i.e. for a single sample).

In order to bring about an optimum utilization of the measuring instruments, it is sometimes of interest to carry out these measurements at several points using the same apparatus. For this purpose, an equipment has been designed, which uses mobile optical components, whose function is to deflect a light beam. This equipment is known from EP-A-177 387 (cf. also U.S. application Ser. No. 4, 820,045).

This known equipment leads to a problem of the reproducibility of the measurements, because the positioning of its mobile optical components is not perfectly reproducible.

SUMMARY OF THE INVENTION

The present invention aims at solving this problem and, according to the invention, for this purpose any movement of the optical component occurring in the orientation of a measurement light beam is eliminated.

More specifically, the present invention relates to a device for optical measurement, particularly by spectrophotometry, which includes: at least one group of optical fibers respectively connected to measuring cells, at least one auxiliary optical fiber, and at least one selection member connecting the auxiliary optical fiber to the group of optical fibers. The selection member selectively establishes an optical link between the auxiliary optical fiber and one of the optical fibers of the group to selectively analyze the light coming from one of the measuring cells, using an analysis means connected to the auxiliary optical fiber or to selectively supply light transmitted by the auxiliary optical fiber to one of the measuring cells. The selection member includes fixed optical means for establishing an optical link between the group of optical fibers and the auxiliary optical fiber and retractable seals respectively associated with the optical fibers of the group and serving to seal the ends of the optical fibers, which lead to the selection member.

In the present invention, the respective paths of the light beams corresponding to the measuring cells are fixed once and for all by design.

The only mobile parts are the seals, which in no way affect the orientation of the light beams. Thus, there is no risk of the device becoming out of adjustment.

Moreover, during a measurement, all the measuring channels except that on which the measurement is taking place, are hidden by the corresponding seals, so that any risk of interference between individual channels is eliminated.

According to a special embodiment of the device according to the invention, the device includes a first auxiliary optical fiber, a first group of optical fibers respectively connected to the measuring cells, a first selection member connecting the first auxiliary optical fiber to the first group, a second group of optical fibers respectively connected to the measuring cells, a second auxiliary optical fiber, a second selection member connecting said second auxiliary fiber to the second group, and means for the simultaneous control of the seals of the first and second selection members. The control means is so as to be able to simultaneously retract the seals corresponding to a measuring cell to supply through the latter a light transmitted by the first auxiliary optical fiber to recover the light passing out of the cell by means of the second auxiliary optical fiber with a view to analyzing the light.

The fixed optical means can include a plurality of fixed optics respectively associated with the optical fibers of the corresponding group and which are able to transform divergent light beams coming from the optical fibers into light beams having parallel rays and a fixed optical system able to focus the light beams with parallel rays onto the end of the corresponding auxiliary optical fiber.

The invention is described in greater detail hereinafter relative to nonlimitative embodiments and with reference to the attached drawings, wherein show:

DETAILED DESCRIPTION OF THE PREFERRED EMBODIMENTS

Figure 1:
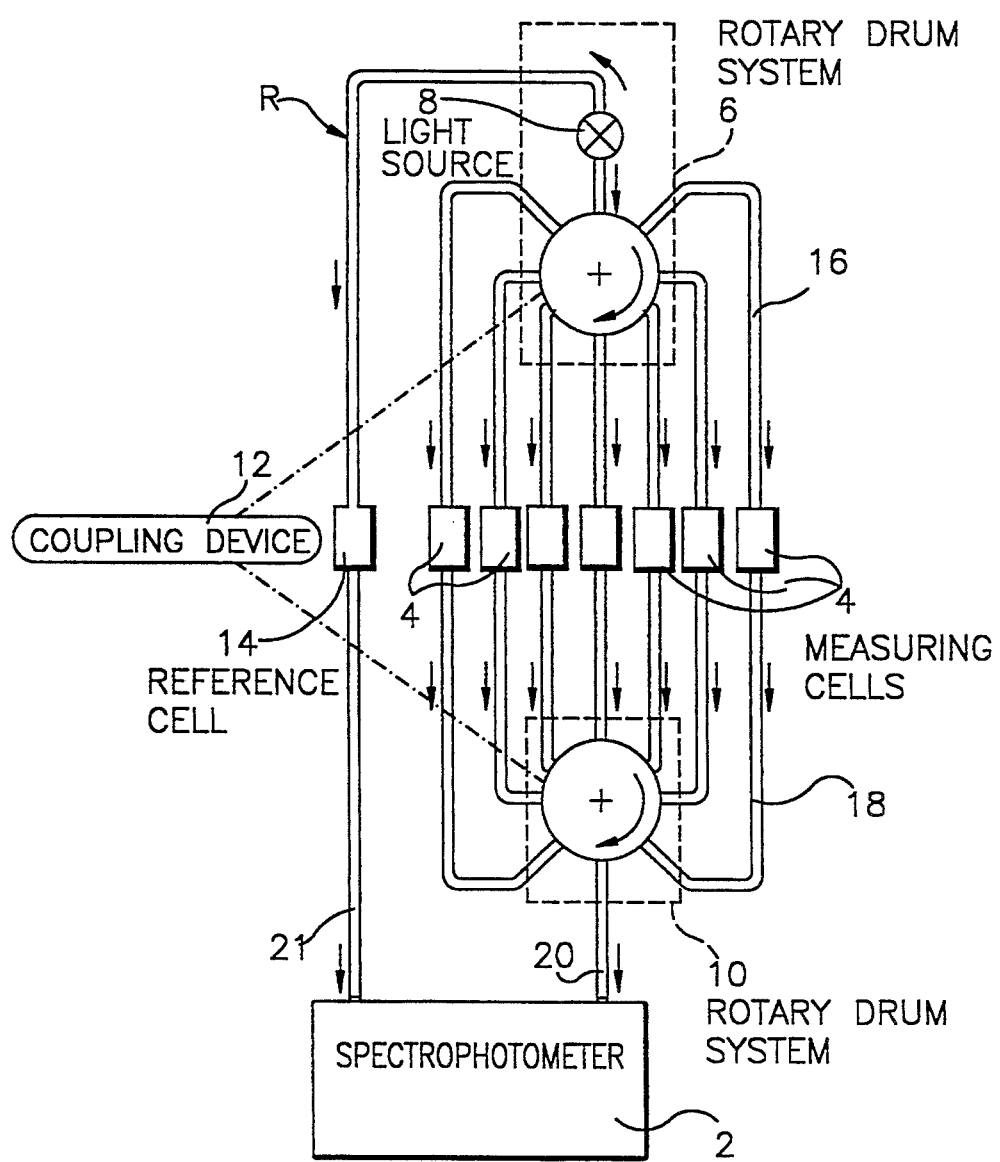
FIG. 1 A diagrammatic view of prior art equipment making it possible to perform measurements at several points.
Figure 3:
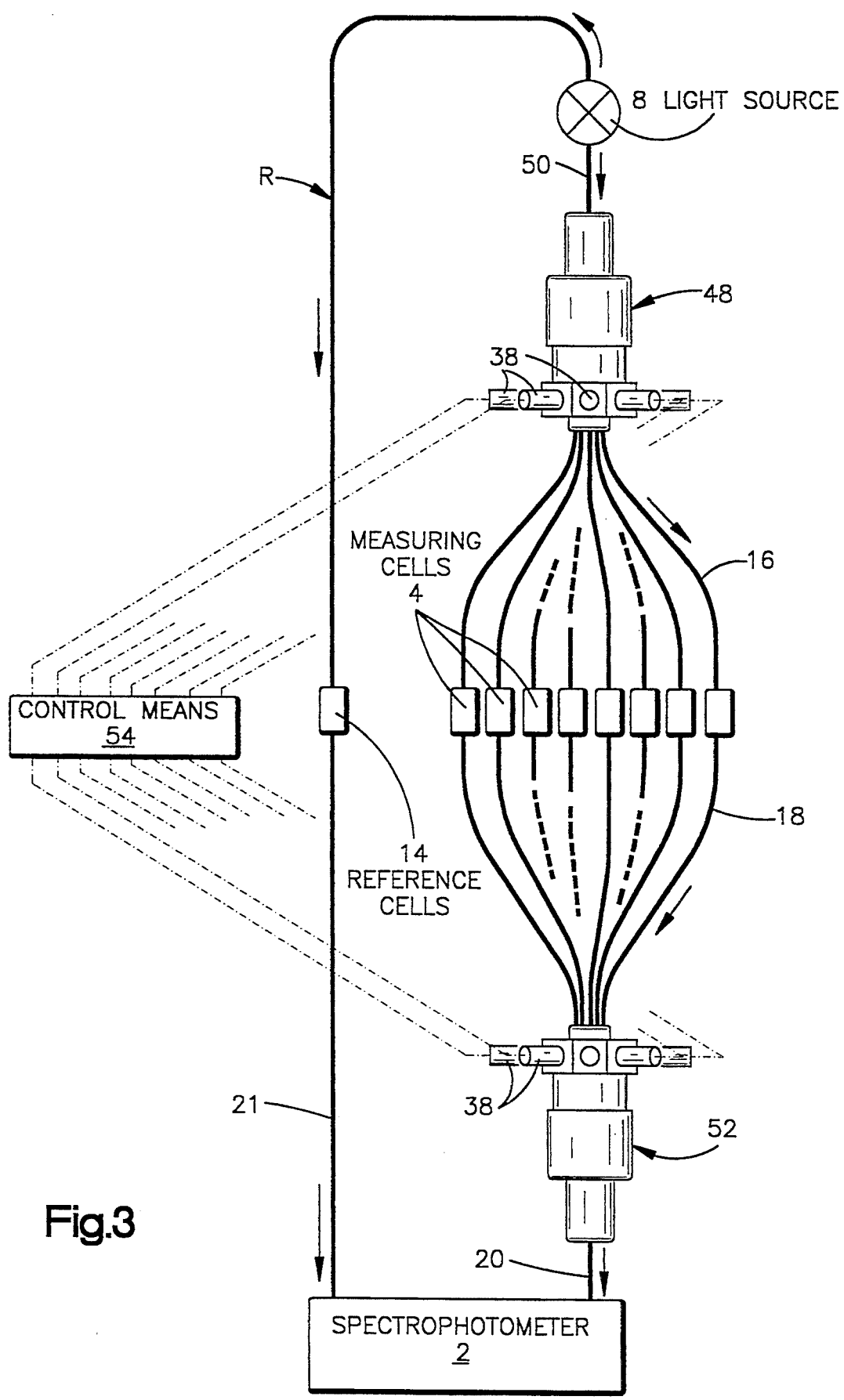
FIG. 3 A diagrammatic view of another embodiment of the device according to the invention.

FIG. 1 is a diagrammatic view of prior art equipment making it possible, using a standard commercial spectrophotometer 2, to monitor in sequential manner the measuring cells 4 with the aid of two drum-type rotary systems, which are described in the document referred to hereinbefore (FIG. 1 of the present application corresponding to FIG. 3 of said document).

The first drum system 6 has a light source 8 and the second drum system 10 has no light source. These two rotary drum systems 6 and 10 are fitted back to back on a same rotation shaft and therefore are mechanically coupled in rotation by a device 12.

The reference channel R permanently illuminates the reference cell 14 used for checking turbidity and the rotary system 6 switches the light successively to one of the optical fibers 16, each leading to one of the measuring cells 4.

On leaving the latter, the optical fibers 18 deliver the light to the second rotary system 10 and then at the outlet of the latter to the measuring channel 20 of the spectrophotometer 2.

As can be seen in FIG. 1, the two drum-type rotary systems 6 and 10, which are coupled in rotation sequentially ensure the light continuity of one of the measuring channels between the emitting source 8 and the measuring channel 20 of the spectrophotometer 2.

Each of the two systems 6 and 10 is traversed by the light in opposite directions, because the inlets of one exactly correspond to the outlets of the other.

FIG. 1 shows the reference channel 21 of the spectrophotometer 2, which receives the light from the reference cell 14.

Figure 2:
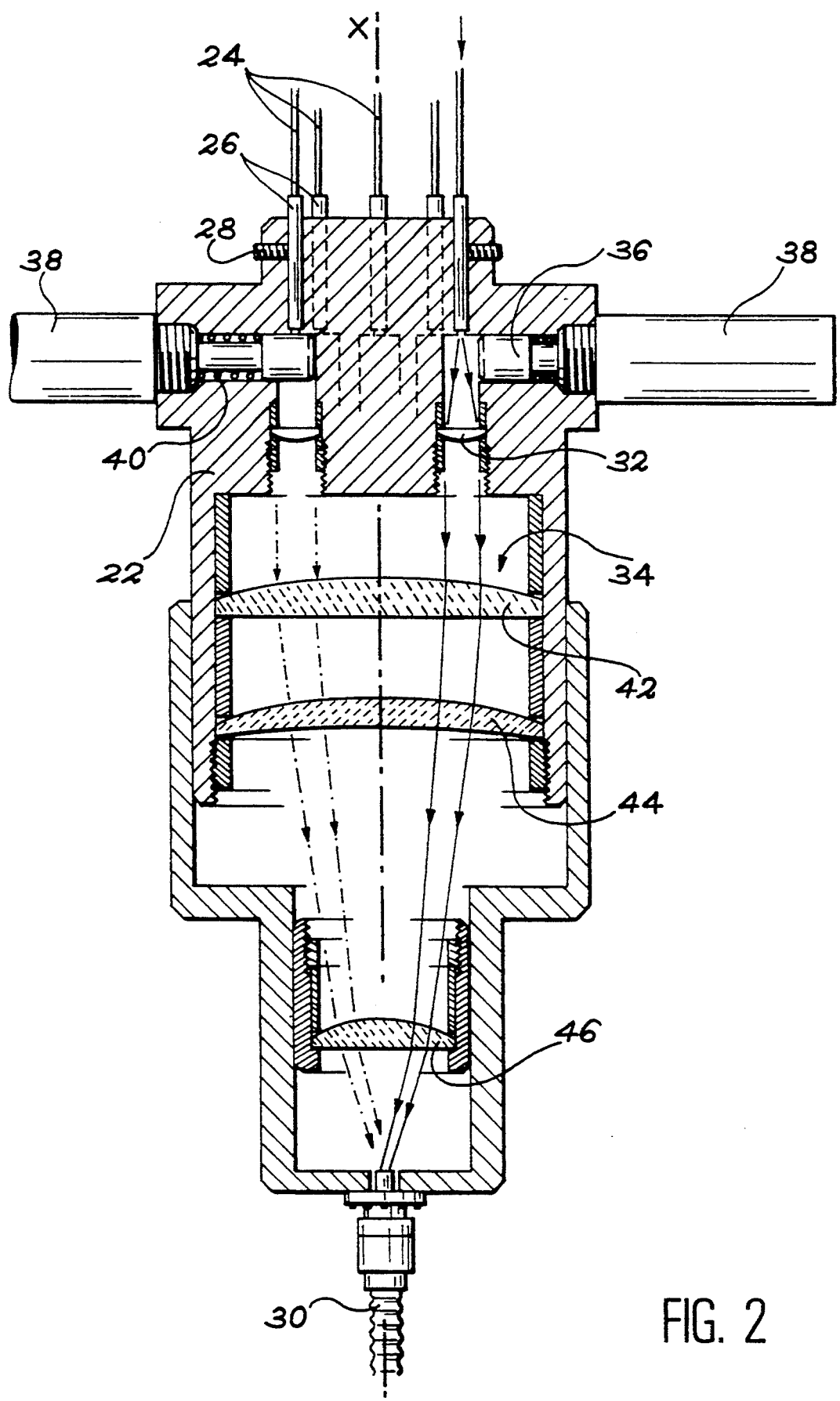
FIG. 2 A diagrammatic view of a special embodiment of the optical measuring device according to the invention.

The device according to the invention and which is diagrammatically shown in FIG. 2 comprises a cylindrical box or case 22, whose axis is designated X.

Optical fibers 24 able to transport light beams from not shown measuring cells are provided at their ends with sleeves 26, which are parallel to the axis X, equidistant with respect to the latter and fixed to one face of the box 22 by means of screws 28, as can be seen in FIG. 2.

The device shown in FIG. 2 also comprises an auxiliary optical fiber 30 fixed to the opposite face of the box 22 and whose axis coincides with the axis X of said box 22.

The device of FIG. 2 also has fixed optics 32, which are e.g. planoconvex lenses and which are provided for transforming into beams with parallel rays the divergent beams from the optical fibers 24.

These optics 32 are respectively associated with the optical fibers 24 and are all placed in the box 22, in the same plane perpendicular to the axis X of said box and equidistant of said axis X.

Within the box 22, the device of FIG. 2 also has a fixed optical system 34, whose optical axis is also the axis X and which is placed between the optics 32 and the auxiliary optical fiber 30. The function of the optical system 34 is to focus the light beams with parallel rays from the optics 32 onto the end face of the auxiliary optical fiber 30.

In such a configuration, all the light signals emitted by the optical fibers 24 are propagated into the auxiliary optical fiber 30 or the output optical fiber.

According to the invention, the device of FIG. 2 also has seals 36, which are respectively associated with the optical fibers 24 and which make it possible to analyze a single signal. Each seal 36 is placed between the end face of the corresponding optical fiber 24 and the corresponding optics 32.

Moreover, said seals 36 are respectively controlled by appropriate means, such as e.g. electromagnets 38 which, when they receive electric activation currents from appropriate, not shown control means, retract the corresponding seals 36, whereas when said electromagnets 38 are deactivated, the seals 36 reassume their positions in which the end faces of the fibers 24 are hidden.

FIG. 2 shows springs 40, which force the seals 36 into their hiding positions when the corresponding electromagnets are deactivated, whereas when they are activated, the seals 36 are spaced from the end faces of the corresponding optical fibers and the springs 40 are compressed.

In order to perform a measurement on a channel corresponding to one of the optical fibers 24, the faces of the ends of the other fibers 24 are hidden or obscured by means of the corresponding seals 36, while permitting the retraction of the seal corresponding to the fiber with which the measurement is performed and, when said measurement has taken place, the face of the end of said fiber is obscured and the seal 36 of one of the other fibers 24 is retracted in order to perform a measurement with the latter and so on.

In the embodiment shown in FIG. 2, the optical system 34 successively comprises a planoconvex lens 42 positioned facing the optics 32, a meniscus lens 44 and another planoconvex lens 46 positioned facing the end face of the auxiliary optical fiber 30, the lenses 42, 44 and 46 having the axis X as the common optical axis.

In a not shown variant, the planoconvex lens 42 is replaced by an optical doublet.

Each of the optics 32 could also be constituted by an optical doublet instead of a planoconvex lens.

Taking account of the principle of the inverse return of the light, it is clear that the device shown in FIG. 2 can be used in the opposite direction and in this case it is the fiber 30 which is the input fiber and the fibers 24 which are the output fibers.

More specifically, the device according to FIG. 2 is usable for supplying light from the optical fiber 30, selectively into the optical fibers 24, which are still connected to the measuring cells, so that only one of these cells receives the light from the optical fiber 30 by means of the optical system 34 and the corresponding optics 32, the corresponding seal 36 being retracted, whereas the other seals 36 seal the end faces of the other optical fibers 24.

The device according to the invention diagrammatically shown in FIG. 3 is the homolog of the equipment diagrammatically shown in FIG. 1, but in the case of FIG. 3 the rotary systems are replaced by selection members according to FIG. 2 (and in the example of FIG. 3 there are eight measuring cells, whereas there are only seven in FIG. 1).

More specifically, FIG. 3 shows a first selection member 48 receiving, by means of an optical fiber 50, the light from the source 8 and which makes it possible to selectively orient said light towards one of the optical fibers 16, so that said light reaches one of the measuring cells 4 and is then propagated into the corresponding optical fiber 18 so as to reach a second selection member 52, Whose seals are positioned in such a way as to enable said light to reach the output optical fiber 20 corresponding thereto and then the spectrophotometer 2.

The device diagrammatically shown in FIG. 3 also has control means 54 for the different electromagnets 38 used and whose seals are normally closed.

In order to perform a measurement on one of the measuring channels, two of the electromagnets are activate with the control means 54, said electromagnets respectively belonging to the selection members 48 and 52 and correspond to the selected measuring channel.

Thus, the corresponding seals are retracted and the light emitted by the source 8 reaches the optical fiber 20 and therefor the spectrophotometer 2 on passing through the corresponding measuring cell 4.

We claim:

1. A Device for optical measurement, particularly by spectrophotometry, comprising:

at least one source of light;

a plurality of measuring cells optically connected to said source of light;

analysis means optically connected to said measuring cells and said source of light;

at least one group of optical fibers (24, 16, 18) respectively connected to said measuring cells (4);

at least one auxiliary optical fiber (30, 50, 20); and at least one selection member (48, 52) connecting said auxiliary optical fiber to said group of optical fibers and selectively establishing an optical link between said auxiliary optical fiber and an optical fiber of said group of optical fibers to selectively pass light from said source of light to said analysis means through an associated one of said measuring cells, said selection member including fixed optical means (32, 34) for establishing an optical link between the group of optical fibers (24, 16, 18) and the auxiliary optical fiber (30, 50, 20) and retractable seals (36) respectively associated with each optical fiber of the group of optical fibers and adapted to seal ends of said group of optical fibers.

2. The device according to claim 1, wherein said fixed optical means includes a plurality of fixed optics (32) respectively associated with each optical fiber (24) of said group of optical fibers and adapted to transform divergent light beams coming from said group of optical fibers into light beams having parallel rays, and a fixed optical system (34) adapted to focus said light beams with parallel rays onto an end of said auxiliary optical fiber (30).

3. The device according to claim 1, wherein a first one of said at least one auxiliary fiber is optically connected to said source of light, a first one of said at least one group of optical fibers is respectively connected to said measuring cells, a first one of said at least one selection member is connecting said first auxiliary optical fiber to said first group of optical fibers, a second one of said at least one group of optical fibers is respectively connected to said measuring cells, a second one of said at least one auxiliary optical fiber is optically connected to said analysis means, a second one of said at least one selection member is connecting said second auxiliary fiber to said second group of optical fibers, and said device further comprises means for simultaneously controlling said seals of said first and second selection members so as to be able to simultaneously retract seals corresponding to a selected one of said measuring cells to supply said light from said first auxiliary optical to said second auxiliary fiber through said selected one of said measuring cells.

4. A device for optical measurement, particularly by spectrophotometry, comprising:

a source of light;

a first auxiliary fiber (50) optically connected to said source of light;

a plurality of measuring cells;

a first group of optical fibers (16) respectively connected to said measuring cells (4);

a first selection member (48) connecting said first auxiliary optical fiber (50) to said first group of optical fibers;

a second group of optical fibers (18) respectively connected to said measuring cells (4);

a second auxiliary optical fiber (20);

a second selection member (52) connecting said second auxiliary fiber (20) to said second group of optical fibers;

said first selection member and said second selection member each including fixed optical means (32, 34) for establishing an optical link between a corresponding one of said first and second groups of optical fibers (24, 16, 18) and a corresponding one of said first and second auxiliary optical fibers (30, 50, 20) and retractable seals (36) respectively associated with each optical fiber of the corresponding group of optical fibers and adapted to seal ends of the corresponding group of optical fibers;

means (54) for simultaneously controlling said seals (36) of said first (48) and second (52) selection members to simultaneously retract seals corresponding to a selected one of said measuring cells to supply said light from said first auxiliary optical fiber to said second auxiliary optical through said selected one of said measuring cells; and analysis means optically connected to said second auxiliary fiber and said source of light for analyzing said light passing through said selected one of said measuring cells.

5. The device according to claim 4, wherein said fixed optical means includes a plurality of fixed optics respectively associated with each optical fiber of a corresponding one of said first and second groups of optical fibers and adapted to transform divergent light beams coming from said corresponding one of said first and second groups of optical fibers into light beams having parallel rays, and a fixed optical system adapted to focus said light beams with parallel rays onto an end of a corresponding one of said first and second auxiliary optical fibers.

* * * * *

UNITED STATES PATENT AND TRADEMARK OFFICE
CERTIFICATE OF CORRECTION

PATENT NO. : 5,450,194                          Page 1 of 2

DATED      : September 12, 1995

INVENTOR(S): Dureault et al.

It is certified that error appears in the above-identified patent and that said Letters Patent is hereby corrected as shown below:

On title page, the following information should be inserted with respect to the assignee: --Commissariat A L'Energie Atomique, Paris, France; and Compagnie Generale Des Matieres Nucleaires, Velizy Villacoublay, France--

On title page, the following information should be inserted with respect to the Attorney, Agent or Firm: --Pearne, Gordon, McCoy & Granger--.

Item [57], in the abstract, line 6, after "member" insert --selectively--.

Column 1, line 38, delete "Ser. No." and insert --Pat. No.--; and
        line 51, delete "includes:" and insert --includes--.

Column 2, line 23, delete "so as to be";
        before line 38, insert the centered heading --BRIEF DESCRIPTION OF THE DRAWINGS--; and
        line 42, delete the centered heading "BRIEF DESCRIPTION OF THE DRAWINGS".

UNITED STATES PATENT AND TRADEMARK OFFICE
CERTIFICATE OF CORRECTION

PATENT NO. : 5,450,194

DATED : September 12, 1995

INVENTOR(S) : Dureault et al.

It is certified that error appears in the above-identified patent and that said Letters Patent is hereby corrected as shown below:

Column 4, line 50, delete "Whose" and insert --whose--; and line 66, (Claim 1, line 1) delete "Device" and insert --device--.

Signed and Sealed this

Twenty-sixth Day of March, 1996

Attest:

BRUCE LEHMAN

*Attesting Officer*     *Commissioner of Patents and Trademarks*